(12) United States Patent
Palmer

(10) Patent No.: US 7,959,647 B2
(45) Date of Patent: *Jun. 14, 2011

(54) SELF FURLING UMBRELLA FRAME FOR CAROTID FILTER

(75) Inventor: Olin Palmer, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 529 days.

This patent is subject to a terminal disclaimer.

(21) Appl. No.: 11/951,476

(22) Filed: Dec. 6, 2007

(65) Prior Publication Data

US 2008/0077175 A1    Mar. 27, 2008

Related U.S. Application Data (60) Division of application No. 10/693,050, filed on Oct. 24, 2003, now Pat. No. 7,306,619, which is a continuation of application No. 09/944,953, filed on Aug. 30, 2001, now Pat. No. 6,638,294.

(51) Int. Cl.
*A61M 29/00* (2006.01)

(52) U.S. Cl. ...................................... 606/200

(58) Field of Classification Search .................. 606/113, 606/114, 127, 159, 200
See application file for complete search history.

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |

(Continued)

FOREIGN PATENT DOCUMENTS

EP    0427429 A3    9/1991

(Continued)

*Primary Examiner* — Kevin T Truong
(74) *Attorney, Agent, or Firm* — Fulwider Patton, LLP; Abbott Vascular; Jonathan Feuchtwang (57) ABSTRACT

A capture device for removal of clots and foreign bodies from vasculature or filtering of particulate from blood flow. The parachute-like capture device is connected to an elongate wire located within a longitudinally elongated tubular member. The invention provides a capture device that is radially expandable and a method for refolding the capture device into a reduced profile during contraction. Thereby, providing an atraumatic retraction of the capture device from within the vasculature.

29 Claims, 3 Drawing Sheets

U.S. PATENT DOCUMENTS

| | | | |
|---|---|---|---|
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 * | 2/2002 | Brooks et al. ................. 606/200 |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsguita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |

| Patent | Kind | Date | Inventor |
|---|---|---|---|
| 6,391,044 | B1 | 5/2002 | Yadav et al. |
| 6,394,978 | B1 | 5/2002 | Boyle et al. |
| 6,395,014 | B1 | 5/2002 | Macoviak et al. |
| 6,398,756 | B2 | 6/2002 | Peterson et al. |
| 6,402,771 | B1 | 6/2002 | Palmer et al. |
| 6,406,471 | B1 | 6/2002 | Jang et al. |
| 6,423,032 | B2 | 7/2002 | Parodi |
| 6,423,086 | B1 | 7/2002 | Barbut et al. |
| 6,425,909 | B1 | 7/2002 | Dieck et al. |
| 6,428,559 | B1 | 8/2002 | Johnson |
| 6,432,122 | B1 | 8/2002 | Gilson et al. |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,450,989 | B2 | 9/2002 | Dubrul et al. |
| 6,458,139 | B1 | 10/2002 | Palmer et al. |
| 6,461,370 | B1 | 10/2002 | Gray et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,497 | B2 | 11/2002 | Wensel et al. |
| 6,485,500 | B1 | 11/2002 | Kokish et al. |
| 6,485,501 | B1 | 11/2002 | Green |
| 6,485,502 | B2 | 11/2002 | Don Michael et al. |
| 6,485,507 | B1 | 11/2002 | Walak et al. |
| 6,494,895 | B2 | 12/2002 | Addis |
| 6,499,487 | B1 | 12/2002 | McKenzie et al. |
| 6,500,166 | B1 | 12/2002 | Zadno Azizi et al. |
| 6,506,203 | B1 | 1/2003 | Boyle et al. |
| 6,506,205 | B2 | 1/2003 | Goldberg et al. |
| 6,511,492 | B1 | 1/2003 | Rosenbluth |
| 6,511,496 | B1 | 1/2003 | Huter et al. |
| 6,511,497 | B1 | 1/2003 | Braun et al. |
| 6,511,503 | B1 | 1/2003 | Burkett et al. |
| 6,514,273 | B1 | 2/2003 | Voss et al. |
| 6,517,550 | B1 | 2/2003 | Konya et al. |
| 6,517,559 | B1 | 2/2003 | O'Connell |
| 6,520,978 | B1 | 2/2003 | Blackledge et al. |
| 6,527,746 | B1 | 3/2003 | Oslund et al. |
| 6,527,791 | B2 | 3/2003 | Fisher |
| 6,530,939 | B1 | 3/2003 | Hopkins et al. |
| 6,530,940 | B2 | 3/2003 | Fisher |
| 6,533,800 | B1 | 3/2003 | Barbut |
| 6,537,294 | B1 | 3/2003 | Boyle et al. |
| 6,537,295 | B2 | 3/2003 | Peterson |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,768 | B1 | 4/2003 | Diaz et al. |
| 6,544,276 | B1 | 4/2003 | Azizi |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,268 | B1 | 4/2003 | Kaganov et al. |
| 6,551,341 | B2 | 4/2003 | Boylan et al. |
| 6,551,342 | B1 | 4/2003 | Shen et al. |
| 6,558,401 | B1 | 5/2003 | Azizi |
| 6,558,405 | B1 | 5/2003 | McInnes |
| 6,562,058 | B2 | 5/2003 | Seguin |
| 6,565,591 | B2 | 5/2003 | Kelly et al. |
| 6,569,184 | B2 | 5/2003 | Huter |
| 6,575,995 | B1 | 6/2003 | Huter et al. |
| 6,575,996 | B1 | 6/2003 | Denison et al. |
| 6,575,997 | B1 | 6/2003 | Palmer et al. |
| 6,582,447 | B1 | 6/2003 | Patel et al. |
| 6,582,448 | B1 | 6/2003 | Boyle et al. |
| 6,585,756 | B1 | 7/2003 | Strecker |
| 6,589,263 | B1 | 7/2003 | Hopkins et al. |
| 6,589,265 | B1 | 7/2003 | Palmer et al. |
| 6,592,546 | B1 | 7/2003 | Barbut et al. |
| 6,592,606 | B2 | 7/2003 | Huter et al. |
| 6,592,607 | B1 | 7/2003 | Palmer et al. |
| 6,592,616 | B1 | 7/2003 | Stack et al. |
| 6,596,011 | B2 | 7/2003 | Johnson et al. |
| 6,599,307 | B1 | 7/2003 | Huter et al. |
| 6,599,308 | B2 | 7/2003 | Amplatz |
| 6,602,269 | B2 | 8/2003 | Wallace et al. |
| 6,602,271 | B2 * | 8/2003 | Adams et al. ............... 606/200 |
| 6,602,272 | B2 | 8/2003 | Boylan et al. |
| 6,602,273 | B2 | 8/2003 | Marshall |
| 6,605,102 | B1 | 8/2003 | Mazzocchi et al. |
| 6,605,111 | B2 | 8/2003 | Bose et al. |
| 6,607,506 | B2 | 8/2003 | Kletschka |
| 6,610,077 | B1 | 8/2003 | Hancock et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita et al. |
| 6,620,182 | B1 | 9/2003 | Khosravi |
| 6,623,450 | B1 | 9/2003 | Dutta |
| 6,629,953 | B1 | 10/2003 | Boyd |
| 6,632,236 | B2 | 10/2003 | Hogendijk |
| 6,632,241 | B1 | 10/2003 | Hancock et al. |
| 6,635,068 | B1 | 10/2003 | Dubrul et al. |
| 6,635,070 | B2 | 10/2003 | Leeflang et al. |
| 6,638,293 | B1 | 10/2003 | Makowner et al. |
| 6,638,294 | B1 | 10/2003 | Palmer |
| 6,645,220 | B1 | 11/2003 | Huter et al. |
| 6,645,221 | B1 | 11/2003 | Richter |
| 6,645,223 | B2 | 11/2003 | Boyle et al. |
| 6,645,224 | B2 | 11/2003 | Gilson et al. |
| 6,652,480 | B1 | 11/2003 | Imran et al. |
| 6,652,505 | B1 | 11/2003 | Tsugita et al. |
| 6,652,554 | B1 | 11/2003 | Wholey et al. |
| 6,652,557 | B1 | 11/2003 | MacDonald |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,673,090 | B2 | 1/2004 | Root et al. |
| 6,676,666 | B2 | 1/2004 | Vrba et al. |
| 6,676,682 | B1 | 1/2004 | Tsugita et al. |
| 6,676,683 | B1 | 1/2004 | Addis |
| 6,679,902 | B1 | 1/2004 | Boyle et al. |
| 6,679,903 | B2 | 1/2004 | Kurz |
| 6,682,546 | B2 | 1/2004 | Amplatz |
| 6,685,722 | B2 | 2/2004 | Rosenbluth et al. |
| 6,689,151 | B2 | 2/2004 | Becker et al. |
| 6,692,513 | B2 | 2/2004 | Streeter et al. |
| 6,695,813 | B1 | 2/2004 | Boyle et al. |
| 6,695,858 | B1 | 2/2004 | Dubrul et al. |
| 6,695,864 | B2 | 2/2004 | Macoviak et al. |
| 6,696,666 | B2 | 2/2004 | Merdan et al. |
| 6,699,260 | B2 | 3/2004 | Dubrul et al. |
| 6,702,834 | B1 | 3/2004 | Boyle et al. |
| 6,706,055 | B2 | 3/2004 | Douk et al. |
| 6,712,834 | B2 | 3/2004 | Yassour et al. |
| 6,712,835 | B2 | 3/2004 | Mazzocchi et al. |
| 6,716,231 | B1 * | 4/2004 | Rafiee et al. ............... 606/200 |
| 6,723,085 | B2 | 4/2004 | Jang et al. |
| 6,726,701 | B2 | 4/2004 | Gilson |
| 6,726,702 | B2 | 4/2004 | Khosravi |
| 6,726,703 | B2 | 4/2004 | Broome et al. |
| 6,740,061 | B1 | 5/2004 | Oslund et al. |
| 6,743,247 | B1 | 6/2004 | Levinson et al. |
| 6,746,469 | B2 | 6/2004 | Mouw |
| 6,752,819 | B1 | 6/2004 | Brady et al. |
| 6,755,846 | B1 | 6/2004 | Yadav |
| 6,758,855 | B2 | 7/2004 | Fulton, III et al. |
| 6,761,727 | B1 | 7/2004 | Ladd |
| 6,773,448 | B2 | 8/2004 | Kusleika et al. |
| 6,790,219 | B1 | 9/2004 | Murphy |
| 6,793,666 | B2 | 9/2004 | Hansen et al. |
| 6,793,668 | B1 | 9/2004 | Fisher |
| 6,800,080 | B1 | 10/2004 | Bates |
| 6,814,739 | B2 | 11/2004 | Secrest et al. |
| 6,818,006 | B2 | 11/2004 | Douk et al. |
| 6,837,898 | B2 | 1/2005 | Boyle |

| | | | | | |
|---|---|---|---|---|---|
| 6,840,950 B2 | 1/2005 | Stanford et al. | 7,048,752 B2 | 5/2006 | Mazzocchi |
| 6,843,798 B2 | 1/2005 | Kusleika et al. | 7,048,758 B2 | 5/2006 | Boyle et al. |
| 6,846,316 B2 | 1/2005 | Abrams | 7,056,328 B2 | 6/2006 | Arnott |
| 6,846,317 B1 | 1/2005 | Nigon | 7,060,082 B2 | 6/2006 | Goll et al. |
| 6,863,696 B2 | 3/2005 | Kantsevitcha et al. | 7,077,854 B2 | 7/2006 | Khosravi |
| 6,866,677 B2 | 3/2005 | Douk et al. | 7,094,243 B2 | 8/2006 | Mulholland |
| 6,872,216 B2 | 3/2005 | Daniel et al. | 7,094,249 B1 | 8/2006 | Broome et al. |
| 6,878,151 B2 | 4/2005 | Carrison et al. | 7,097,440 B2 | 8/2006 | Papp et al. |
| 6,878,153 B2 | 4/2005 | Linder et al. | 7,097,651 B2 | 8/2006 | Harrison et al. |
| 6,887,256 B2 | 5/2005 | Gilson et al. | 7,101,379 B2 | 9/2006 | Gregory, Jr. et al. |
| 6,887,257 B2 | 5/2005 | Salaheih et al. | 7,101,380 B2 | 9/2006 | Khachin et al. |
| 6,887,258 B2 | 5/2005 | Denison | 7,108,707 B2 | 9/2006 | Huter et al. |
| 6,888,098 B1 | 5/2005 | Merdan et al. | 2002/0091408 A1 | 7/2002 | Sutton et al. |
| 6,890,340 B2 | 5/2005 | Duane | 2002/0091409 A1 | 7/2002 | Sutton et al. |
| 6,890,341 B2 | 5/2005 | Dieck et al. | 2002/0095141 A1 | 7/2002 | Belef et al. |
| 6,893,450 B2 | 5/2005 | Foster | 2002/0099407 A1 | 7/2002 | Becker et al. |
| 6,893,451 B2 | 5/2005 | Cano et al. | 2002/0103501 A1 | 8/2002 | Diaz et al. |
| 6,896,690 B1 | 5/2005 | Lambrecht et al. | 2002/0107541 A1 | 8/2002 | Vale et al. |
| 6,896,691 B2 | 5/2005 | Boylan | 2002/0111648 A1 | 8/2002 | Kusleika et al. |
| 6,902,540 B2 | 6/2005 | Dorros et al. | 2002/0111649 A1 | 8/2002 | Russo et al. |
| 6,908,474 B2 | 6/2005 | Hogenkijk et al. | 2002/0115942 A1 | 8/2002 | Stanford et al. |
| 6,911,036 B2 | 6/2005 | Douk et al. | 2002/0120286 A1 | 8/2002 | DoBrava et al. |
| 6,913,612 B2 | 7/2005 | Palmer et al. | 2002/0120287 A1 | 8/2002 | Huter |
| 6,918,921 B2 | 7/2005 | Brady et al. | 2002/0121472 A1 | 9/2002 | Garner et al. |
| 6,929,652 B1 | 8/2005 | Andrews | 2002/0123720 A1 | 9/2002 | Kusleika et al. |
| 6,932,830 B2 | 8/2005 | Ungs | 2002/0123755 A1 | 9/2002 | Lowe et al. |
| 6,932,831 B2 | 8/2005 | Forber | 2002/0128679 A1 | 9/2002 | Turovskiy et al. |
| 6,936,058 B2 | 8/2005 | Forde et al. | 2002/0128680 A1 | 9/2002 | Pavlovic |
| 6,936,059 B2 | 8/2005 | Belef | 2002/0128681 A1 | 9/2002 | Broome et al. |
| 6,939,361 B1 | 9/2005 | Kleshinski | 2002/0133092 A1 | 9/2002 | Oslund et al. |
| 6,939,362 B2 | 9/2005 | Boyle et al. | 2002/0138094 A1 | 9/2002 | Borillo et al. |
| 6,942,673 B2 | 9/2005 | Bates et al. | 2002/0138095 A1 | 9/2002 | Mazzocchi et al. |
| 6,949,103 B2 | 9/2005 | Mazzocchi et al. | 2002/0143360 A1 | 10/2002 | Douk et al. |
| 6,951,570 B2 | 10/2005 | Linder et al. | 2002/0143361 A1 | 10/2002 | Douk et al. |
| 6,953,471 B1 | 10/2005 | Lilly et al. | 2002/0151927 A1 | 10/2002 | Douk et al. |
| 6,953,472 B2 | 10/2005 | Palmer et al. | 2002/0156456 A1 | 10/2002 | Fisher |
| 6,958,074 B2 | 10/2005 | Russell | 2002/0156457 A1 | 10/2002 | Fisher |
| 6,960,370 B2 | 11/2005 | Monni et al. | 2002/0161390 A1 | 10/2002 | Mouw |
| 6,962,598 B2 | 11/2005 | Linder et al. | 2002/0161392 A1 | 10/2002 | Dubrul |
| 6,964,670 B1 | 11/2005 | Shah | 2002/0161393 A1 | 10/2002 | Demond et al. |
| 6,964,672 B2 | 11/2005 | Brady | 2002/0161395 A1 | 10/2002 | Douk et al. |
| 6,964,673 B2 | 11/2005 | Tsugita et al. | 2002/0165576 A1 | 11/2002 | Boyle et al. |
| 6,969,395 B2 | 11/2005 | Eskuri | 2002/0169414 A1 | 11/2002 | Kletschka |
| 6,969,396 B2 | 11/2005 | Krolik et al. | 2002/0169458 A1 | 11/2002 | Connors, III |
| 6,969,402 B2 | 11/2005 | Bales et al. | 2002/0169472 A1 | 11/2002 | Douk et al. |
| 6,970,730 B2 | 11/2005 | Fuimaono et al. | 2002/0169474 A1 | 11/2002 | Kusleika et al. |
| 6,972,025 B2 | 12/2005 | WasDyke | 2002/0173815 A1 | 11/2002 | Hogendijk et al. |
| 6,973,340 B2 | 12/2005 | Fuimaono et al. | 2002/0173817 A1 | 11/2002 | Kletschka et al. |
| 6,974,468 B2 | 12/2005 | DoBrava et al. | 2002/0188313 A1 | 12/2002 | Johnson et al. |
| 6,974,469 B2 | 12/2005 | Broome et al. | 2002/0188314 A1 | 12/2002 | Anderson et al. |
| 6,979,343 B2 | 12/2005 | Russo | 2002/0193825 A1 | 12/2002 | McGuckin et al. |
| 6,979,344 B2 | 12/2005 | Jones et al. | 2002/0193826 A1 | 12/2002 | McGuckin et al. |
| 6,986,778 B2 | 1/2006 | Zadno-Azizi | 2002/0193827 A1 | 12/2002 | McGuckin et al. |
| 6,989,019 B2 | 1/2006 | Mazzocchi et al. | 2002/0193828 A1 | 12/2002 | Griffin et al. |
| 6,989,021 B2 | 1/2006 | Bosma et al. | 2003/0004536 A1 | 1/2003 | Boylan et al. |
| 6,989,027 B2 | 1/2006 | Allen et al. | 2003/0004537 A1 | 1/2003 | Boyle et al. |
| 6,991,641 B2 | 1/2006 | Diaz et al. | 2003/0004539 A1 | 1/2003 | Linder et al. |
| 6,991,642 B2 | 1/2006 | Peterson | 2003/0004540 A1 | 1/2003 | Linder et al. |
| RE38,972 E | 2/2006 | Purdy | 2003/0004541 A1 | 1/2003 | Linder et al. |
| 6,994,718 B2 | 2/2006 | Groothuis et al. | 2003/0009188 A1 | 1/2003 | Linder et al. |
| 6,997,938 B2 | 2/2006 | Wang et al. | 2003/0009189 A1 | 1/2003 | Gilson et al. |
| 6,997,939 B2 | 2/2006 | Linder et al. | 2003/0015206 A1 | 1/2003 | Roth et al. |
| 7,001,406 B2 | 2/2006 | Eskuri et al. | 2003/0018354 A1 | 1/2003 | Roth et al. |
| 7,001,407 B2 | 2/2006 | Hansen et al. | 2003/0023265 A1 | 1/2003 | Forber |
| 7,004,954 B1 | 2/2006 | Voss et al. | 2003/0028238 A1 | 2/2003 | Burkett et al. |
| 7,004,955 B2 | 2/2006 | Shen et al. | 2003/0032941 A1 | 2/2003 | Boyle et al. |
| 7,004,956 B2 | 2/2006 | Palmer et al. | 2003/0032977 A1 | 2/2003 | Brady et al. |
| 7,004,964 B2 | 2/2006 | Thompson et al. | 2003/0040772 A1 | 2/2003 | Hyodoh et al. |
| 7,011,671 B2 | 3/2006 | Welch | 2003/0042186 A1 | 3/2003 | Boyle et al. |
| 7,011,672 B2 | 3/2006 | Barbut et al. | 2003/0045898 A1 | 3/2003 | Harrison et al. |
| 7,014,647 B2 | 3/2006 | Brady et al. | 2003/0057156 A1 | 3/2003 | Peterson et al. |
| 7,018,372 B2 | 3/2006 | Casey | 2003/0060782 A1 | 3/2003 | Bose et al. |
| 7,018,385 B2 | 3/2006 | Bates et al. | 2003/0060843 A1 | 3/2003 | Boucher |
| 7,018,393 B1 | 3/2006 | Boyle et al. | 2003/0060844 A1 | 3/2003 | Borillo et al. |
| 7,029,440 B2 | 4/2006 | Broome et al. | 2003/0065354 A1 | 4/2003 | Boyle et al. |
| 7,033,375 B2 | 4/2006 | Mazzocchi et al. | 2003/0069596 A1 | 4/2003 | Eskuri |
| 7,037,320 B2 | 5/2006 | Brady et al. | 2003/0069597 A1 | 4/2003 | Petersen |
| 7,041,116 B2 | 5/2006 | Goto et al. | 2003/0078519 A1 | 4/2003 | Salahieh et al. |
| 7,044,958 B2 | 5/2006 | Douk et al. | 2003/0078614 A1 | 4/2003 | Satahieh et al. |

| | | | | | |
|---|---|---|---|---|---|
| 2003/0083692 A1 | 5/2003 | Vrba et al. | 2004/0049226 A1 | 3/2004 | Keegan et al. |
| 2003/0083693 A1 | 5/2003 | Daniel et al. | 2004/0059372 A1 | 3/2004 | Tsugita |
| 2003/0100917 A1 | 5/2003 | Boyle et al. | 2004/0059373 A1 | 3/2004 | Shapiro et al. |
| 2003/0100918 A1 | 5/2003 | Duane | 2004/0082967 A1 | 4/2004 | Broome et al. |
| 2003/0105484 A1 | 6/2003 | Boyle et al. | 2004/0082968 A1 | 4/2004 | Krolik et al. |
| 2003/0109824 A1 | 6/2003 | Anderson et al. | 2004/0088000 A1 | 5/2004 | Muller |
| 2003/0114879 A1 | 6/2003 | Euteneuer et al. | 2004/0088002 A1 | 5/2004 | Boyle et al. |
| 2003/0114880 A1 | 6/2003 | Hansen et al. | 2004/0093009 A1 | 5/2004 | Denison et al. |
| 2003/0120303 A1 | 6/2003 | Boyle et al. | 2004/0093010 A1 | 5/2004 | Gesswein et al. |
| 2003/0130680 A1 | 7/2003 | Russell | 2004/0093011 A1 | 5/2004 | Vrba |
| 2003/0130681 A1 | 7/2003 | Ungs | 2004/0093012 A1 | 5/2004 | Cully et al. |
| 2003/0130682 A1 | 7/2003 | Broome et al. | 2004/0093013 A1 | 5/2004 | Brady et al. |
| 2003/0130684 A1 | 7/2003 | Brady et al. | 2004/0098022 A1 | 5/2004 | Barone |
| 2003/0130685 A1 | 7/2003 | Daniel et al. | 2004/0098026 A1 | 5/2004 | Joergensen et al. |
| 2003/0130686 A1 | 7/2003 | Daniel et al. | 2004/0098032 A1 | 5/2004 | Papp et al. |
| 2003/0130687 A1 | 7/2003 | Daniel et al. | 2004/0098033 A1 | 5/2004 | Leeflang et al. |
| 2003/0130688 A1 | 7/2003 | Daniel et al. | 2004/0102807 A1 | 5/2004 | Kusleika et al. |
| 2003/0135162 A1 | 7/2003 | Deyette, Jr. et al. | 2004/0106944 A1 | 6/2004 | Daniel et al. |
| 2003/0135232 A1 | 7/2003 | Douk et al. | 2004/0111111 A1 | 6/2004 | Lin |
| 2003/0139764 A1 | 7/2003 | Levinson et al. | 2004/0116960 A1 | 6/2004 | Demond et al. |
| 2003/0144685 A1 | 7/2003 | Boyle et al. | 2004/0122466 A1 | 6/2004 | Bales |
| 2003/0144689 A1 | 7/2003 | Brady et al. | 2004/0127933 A1 | 7/2004 | Demond et al. |
| 2003/0150821 A1 | 8/2003 | Bates et al. | 2004/0127934 A1 | 7/2004 | Gilson et al. |
| 2003/0153935 A1 | 8/2003 | Mialhe | 2004/0127936 A1 | 7/2004 | Salaheih et al. |
| 2003/0153942 A1 | 8/2003 | Wang et al. | 2004/0138693 A1 | 7/2004 | Eskuri et al. |
| 2003/0153943 A1 | 8/2003 | Michael et al. | 2004/0138694 A1 | 7/2004 | Tran et al. |
| 2003/0158574 A1 | 8/2003 | Esch et al. | 2004/0138696 A1 | 7/2004 | Drasler et al. |
| 2003/0171770 A1 | 9/2003 | Kusleika et al. | 2004/0147955 A1 | 7/2004 | Beulke et al. |
| 2003/0171771 A1 | 9/2003 | Anderson et al. | 2004/0153118 A1 | 8/2004 | Clubb et al. |
| 2003/0171803 A1 | 9/2003 | Shimon | 2004/0153119 A1 | 8/2004 | Kusleika et al. |
| 2003/0176884 A1 | 9/2003 | Berrada et al. | 2004/0158275 A1 | 8/2004 | Crank et al. |
| 2003/0176885 A1 | 9/2003 | Broome et al. | 2004/0158277 A1 | 8/2004 | Lowe et al. |
| 2003/0176886 A1 | 9/2003 | Wholey et al. | 2004/0158278 A1 | 8/2004 | Becker et al. |
| 2003/0176889 A1 | 9/2003 | Boyle et al. | 2004/0158279 A1 | 8/2004 | Petersen |
| 2003/0181942 A1 | 9/2003 | Sutton et al. | 2004/0158280 A1 | 8/2004 | Morris et al. |
| 2003/0181943 A1 | 9/2003 | Daniel et al. | 2004/0158281 A1 | 8/2004 | Boyle et al. |
| 2003/0187474 A1 | 10/2003 | Keegan et al. | 2004/0167564 A1 | 8/2004 | Fedie |
| 2003/0187475 A1 | 10/2003 | Tsugita et al. | 2004/0167565 A1 | 8/2004 | Beulke et al. |
| 2003/0187495 A1 | 10/2003 | Cully et al. | 2004/0167566 A1 | 8/2004 | Beulke et al. |
| 2003/0191493 A1 | 10/2003 | Epstein et al. | 2004/0167567 A1 | 8/2004 | Cano et al. |
| 2003/0195554 A1 | 10/2003 | Shen et al. | 2004/0167568 A1 | 8/2004 | Boyle et al. |
| 2003/0195555 A1 | 10/2003 | Khairkhahan et al. | 2004/0172055 A1 | 9/2004 | Huter et al. |
| 2003/0195556 A1 | 10/2003 | Stack et al. | 2004/0176794 A1 | 9/2004 | Khosravi |
| 2003/0199819 A1 | 10/2003 | Beck | 2004/0193208 A1 | 9/2004 | Talpade et al. |
| 2003/0199921 A1 | 10/2003 | Palmer et al. | 2004/0199198 A1 | 10/2004 | Beulke et al. |
| 2003/0204168 A1 | 10/2003 | Bosme et al. | 2004/0199199 A1 | 10/2004 | Krolik et al. |
| 2003/0204202 A1 | 10/2003 | Palmer et al. | 2004/0199203 A1 | 10/2004 | Oslund et al. |
| 2003/0208222 A1 | 11/2003 | Zadno-Azizi | 2004/0204737 A1 | 10/2004 | Boismier et al. |
| 2003/0208224 A1 | 11/2003 | Broome | 2004/0210250 A1 | 10/2004 | Eskuri |
| 2003/0208225 A1 | 11/2003 | Goll et al. | 2004/0220608 A1 | 11/2004 | D'Aquanni et al. |
| 2003/0208226 A1 | 11/2003 | Bruckheimer et al. | 2004/0220609 A1 | 11/2004 | Douk et al. |
| 2003/0208227 A1 | 11/2003 | Thomas | 2004/0220611 A1 | 11/2004 | Ogle |
| 2003/0208228 A1 | 11/2003 | Gilson et al. | 2004/0225322 A1 | 11/2004 | Garrison et al. |
| 2003/0208229 A1 | 11/2003 | Kletschka | 2004/0236368 A1 | 11/2004 | McGuckin, Jr. et al. |
| 2003/0212361 A1 | 11/2003 | Boyle et al. | 2004/0236369 A1 | 11/2004 | Dubrul |
| 2003/0212429 A1 | 11/2003 | Keegan et al. | 2004/0249409 A1 | 12/2004 | Krolik et al. |
| 2003/0212431 A1 | 11/2003 | Brady et al. | 2004/0254601 A1 | 12/2004 | Eskuri |
| 2003/0212434 A1 | 11/2003 | Thielen | 2004/0254602 A1 | 12/2004 | Lehe et al. |
| 2003/0216774 A1 | 11/2003 | Larson | 2004/0260308 A1 | 12/2004 | Gilson et al. |
| 2003/0220665 A1 | 11/2003 | Eskuri et al. | 2004/0260333 A1 | 12/2004 | Dubrul et al. |
| 2003/0225418 A1 | 12/2003 | Esksuri et al. | 2004/0267301 A1 | 12/2004 | Boylan et al. |
| 2003/0225435 A1 | 12/2003 | Huter et al. | 2004/0267302 A1 | 12/2004 | Gilson et al. |
| 2003/0229295 A1 | 12/2003 | Houde et al. | 2005/0004594 A1 | 1/2005 | Nool et al. |
| 2003/0229374 A1 | 12/2003 | Brady et al. | 2005/0004595 A1 | 1/2005 | Boyle et al. |
| 2003/0233117 A1 | 12/2003 | Adams et al. | 2005/0004597 A1 | 1/2005 | McGuckin, Jr. et al. |
| 2003/0236545 A1 | 12/2003 | Gilson | 2005/0010245 A1 | 1/2005 | Wasicek |
| 2004/0002730 A1 | 1/2004 | Denison et al. | 2005/0010246 A1 | 1/2005 | Streeter et al. |
| 2004/0006361 A1 | 1/2004 | Boyle et al. | 2005/0010247 A1 | 1/2005 | Kusleika et al. |
| 2004/0006364 A1 | 1/2004 | Ladd | 2005/0021075 A1 | 1/2005 | Bonnette et al. |
| 2004/0006365 A1 | 1/2004 | Brady et al. | 2005/0021076 A1 | 1/2005 | Mazzocchi et al. |
| 2004/0006366 A1 | 1/2004 | Huter et al. | 2005/0055048 A1 | 3/2005 | Dieck et al. |
| 2004/0006367 A1 | 1/2004 | Johnson et al. | 2005/0070953 A1 | 3/2005 | Riley |
| 2004/0006368 A1 | 1/2004 | Mazzocchi et al. | 2005/0075663 A1 | 4/2005 | Boyle et al. |
| 2004/0015184 A1 | 1/2004 | Boyle et al. | 2005/0080446 A1 | 4/2005 | Gilson et al. |
| 2004/0019363 A1 | 1/2004 | Hanson et al. | 2005/0085842 A1 | 4/2005 | Eversull et al. |
| 2004/0034385 A1 | 2/2004 | Gilson et al. | 2005/0090845 A1 | 4/2005 | Boyd |
| 2004/0039411 A1 | 2/2004 | Gilson et al. | 2005/0090857 A1 | 4/2005 | Kusleika et al. |
| 2004/0044359 A1 | 3/2004 | Renati et al. | 2005/0090858 A1 | 4/2005 | Pavlovic |
| 2004/0044360 A1 | 3/2004 | Lowe | 2005/0096691 A1 | 5/2005 | Groothuis et al. |

| | | |
|---|---|---|
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| EP | 1 127 556 A2 | 8/2001 |
| EP | 1 127 556 A3 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO01/87183 | 11/2001 |

\* cited by examiner

SELF FURLING UMBRELLA FRAME FOR CAROTID FILTER

CROSS-REFERENCE TO RELATED APPLICATIONS

This is a divisional of U.S. Pat. No. 7,306,619, U.S. Ser. No. 10/693,050, filed Oct. 24, 2003 and issuing on Dec. 11, 2007; which is a Continuation application of U.S. Pat. No. 6,638,294, Ser. No. 09/944,953, filed Aug. 30, 2001 and issued Oct. 28, 2003.

BACKGROUND OF THE INVENTION

1. Field of the Invention

This invention relates generally to medical devices used during vascular intervention, and more particularly, concerns medical devices that are useful in treating thromboembolic disorders and for removal of foreign bodies in the vascular system.

2. Description of Related Art

This invention relates generally to medical devices used during vascular intervention, and more particularly, concerns medical devices that are useful in treating thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exists retrieval devices for the removal of foreign bodies, certain of such devices form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another distal vessel.

Various thrombectomy and foreign matter removal devices have been disclosed in the art. However, such devices have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, wherein the pleats extend radially and can obstruct retraction of the device into the microcatheter sheathing.

What has been needed and heretofore unavailable is an extraction device that can be easily and controllably deployed into and retracted from the circulatory system for the effective removal of clots and foreign bodies. There is also a need for a system that can be used as a temporary arterial or venous filter to capture and remove thromboemboli generated during endovascular procedures. Moreover, due to difficult-to-access anatomy such as the cerebral vasculature and the neurovasculature, the invention should possess a small collapsed profile and preferably be expandable to allow the device to be delivered through the lumen of commercially available catheters. The present invention satisfies these needs.

SUMMARY OF THE INVENTION

Briefly, and in general terms, the present invention is directed to an improvement in devices for removing embolic or foreign material from a vessel. In one aspect, the present invention is a medical device which includes an elongate member having a proximal end portion for manipulation by an operator and a distal end portion which is attached to a filter or capture device. This filter or capture device includes a body having a plurality of struts extending from the elongate member to a basket or cage structure. The basket or cage structure includes a proximally directed opening and a generally conical shape in an expanded configuration. When the basket or cage is placed in a compressed or closed configuration pleats are formed in the basket or cage and certain of the struts operate to fold the pleats to thereby define a relatively sleek profile.

In another aspect of the invention, the struts include a first set of arms and a second set of arms, single members of which are interspaced between adjacent pairs of arms of the first set when the medical device is in an expanded configuration. Each of the arms of the second set include a proximal portion defining a slight helix so that when the medical device is compressed radially, the arms of the second set rotate with respect to the arms of the first set. Such action accomplishes the folding or furling of the pleats of the basket or cage. In still another aspect of the invention, each of the arms of the first set also include a proximal portion defining a slight helix so that when the medical device is compressed radially, both the first and second sets of arms rotate with respect to the other.

It is contemplated that the medical device of the present invention can further include an atraumatic distal end portion projecting distally from the cage or basket. Additionally, the cage or basket is defined by various structures including weaved fabrics or interconnected metal struts with or without a membrane extending thereacross.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention is useful for the removal of embolic or foreign material from vasculature. The present invention is intended to be used in various sized vessels and in vessels having varying degrees of tortuosity. Of particular significance is the contemplated use of the preferred embodiment in the highly tortuous cerebral vasculature or neurovasculature. Moreover, the disclosed capture device is characterized by having an expanded structure that is useful as a filter device, and a contracted structure having a low profile folded condition to facilitate an atraumatic delivery and retraction of the system.

Figures 1, 2:
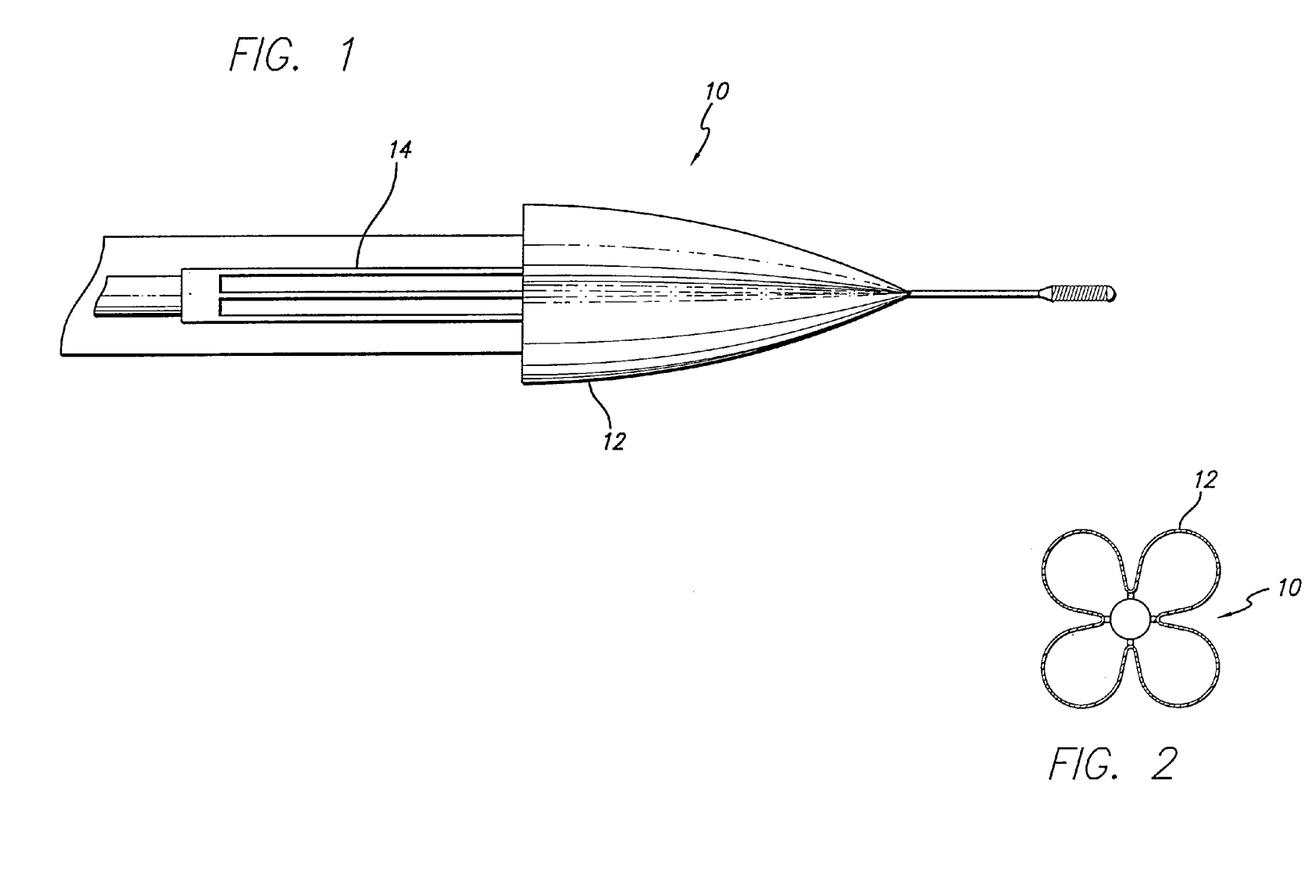
FIG. 1 (prior art) is a partial cross-sectional view depicting an extraction device depicting a collapsed filter device.
FIG. 2 is a end view of the extraction device depicted in FIG. 1.

Referring to FIGS. 1-2, a collapsed and folded capture device 10 existing in the art is depicted having pleats 12 which extend radially when the capture device 10 is in a folded position. As seen in FIG. 1, the radially extended, folded pleats may be problematic when the capture device is retracted within a catheter sheath 14. That is, the pleats may get in the way when retracting the capture device 10 within the sheath 14. This obstruction may result in the re-release of any captured embolic or foreign material back into the vasculature. The present invention solves this problem by improving the folding technique and reducing the cross-sectional profile of the collapsed capture device.

Figure 3:
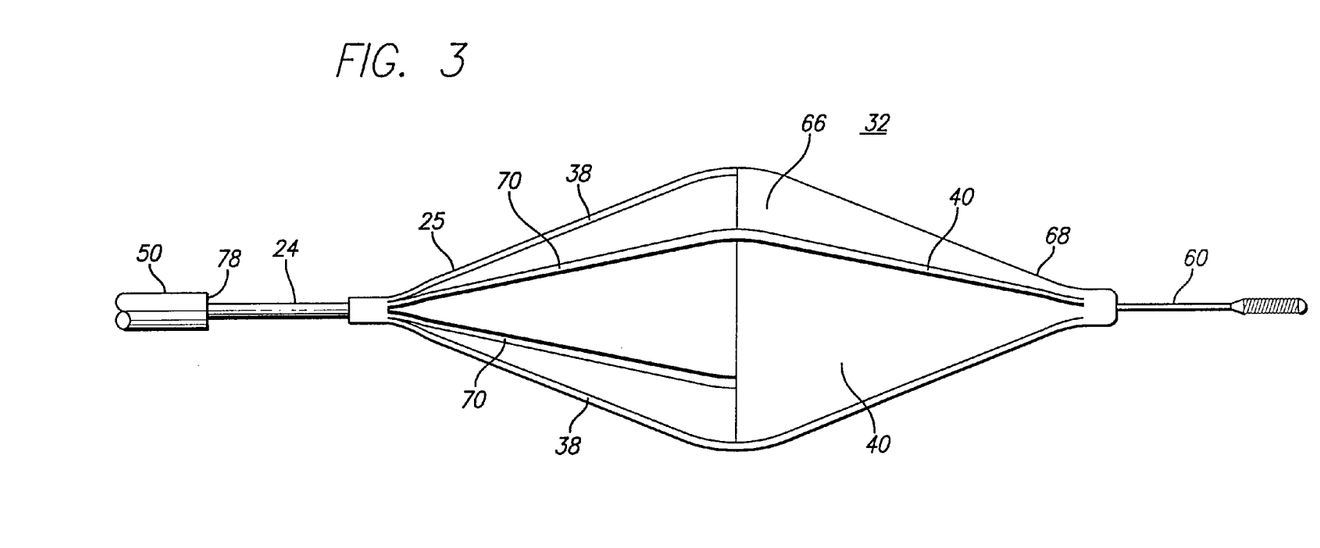
FIG. 3 is a side partial cutaway view of a parachute-like extraction device in an expanded condition.
Figure 4:
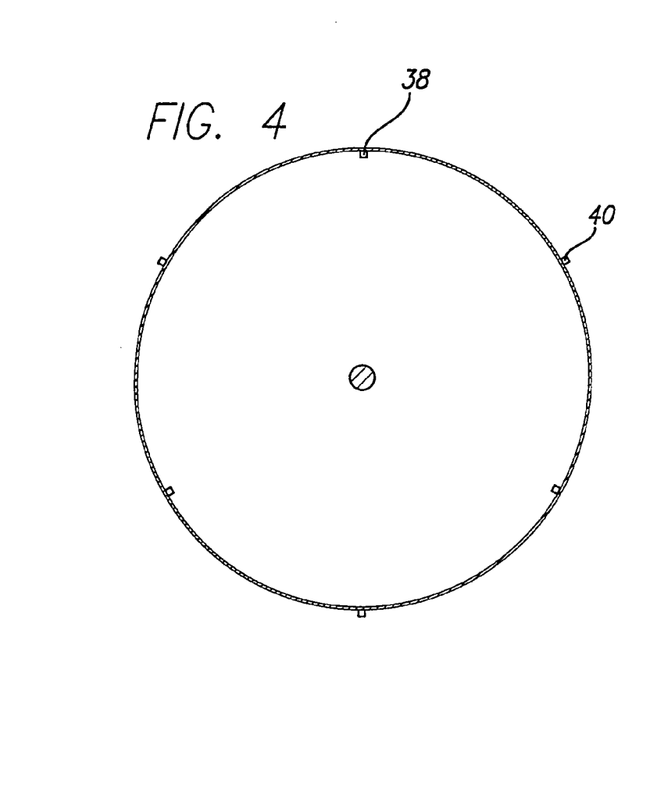
FIG. 4 is a cross-sectional view of the expanded extraction device depicted in FIG. 3.

Referring to FIG. 3, there is shown an embodiment of the present invention, in an expanded condition, which is adapted to capture embolic or foreign material found within a vessel. In a presently preferred first embodiment, a parachute-like capture device 32 includes an elongate wire 24 having a basket or cage 25 attached to a distal end thereof. The cage includes a plurality of struts or structural members 38, 40 extending longitudinally from the elongate wire 24. The elongate wire 24 is configured longitudinally within a delivery catheter 50. The elongate wire 24 can additionally define a tubular structure having an internal lumen. The distal end 60 of the capture device 32 can be defined by an atraumatic tip extending longitudinally and having a generally helical substructure. Alternatively, the tip can be omitted so that the device can be routed over a guidewire.

Figure 5:
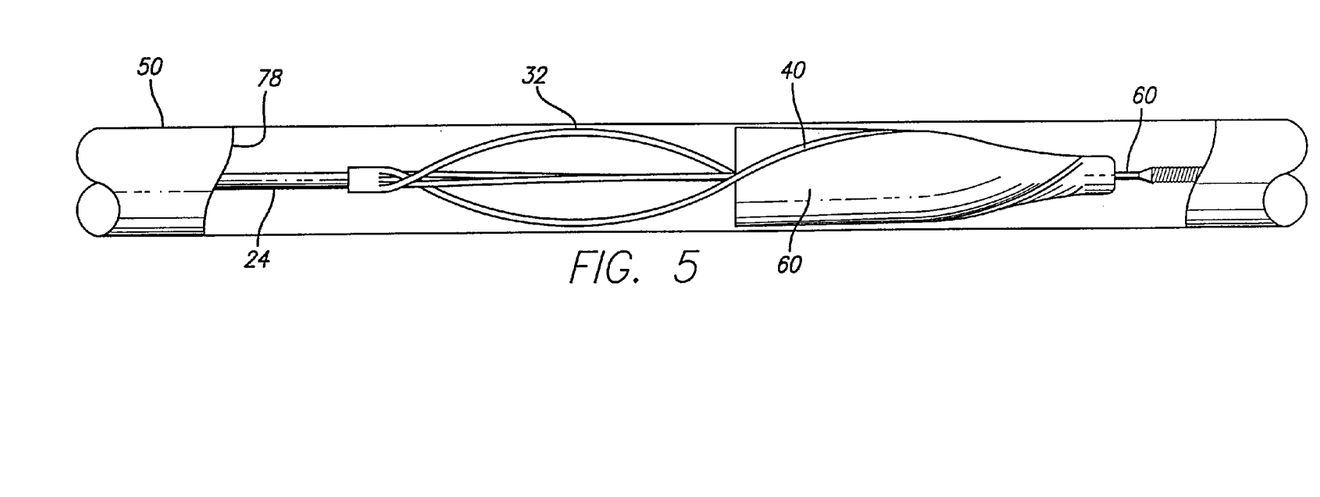
FIG. 5 is a side, cutaway view of the parachute-like extraction device in a collapsed self folded condition within a catheter.
Figure 6:
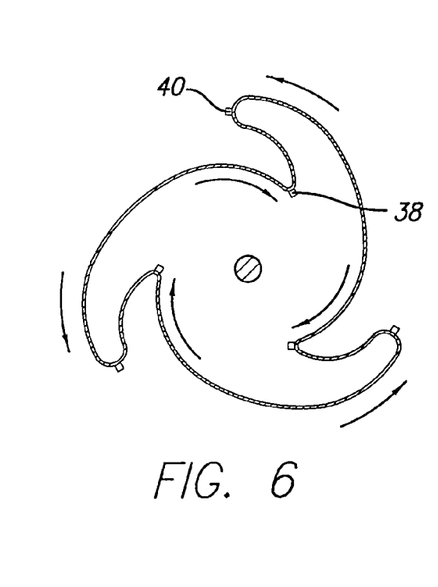
FIG. 6 is a cross-sectional view of a first stage in collapsing the parachute-like extraction device shown in FIG. 4, depicting the helix rotation of the outer structural members relative to the inner structural members.
Figure 7:
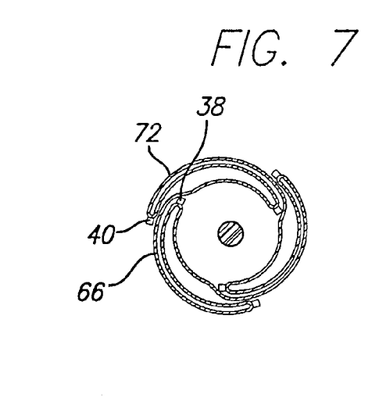
FIG. 7 is a cross-sectional view of a second stage in collapsing the parachute-like extraction device shown in FIG. 4.

The capture device 32 includes a frame having a plurality of structural members 38, 40. The plurality of structural members 38, 40 embody a plurality of inner structural members 38 and a plurality of outer structural members 40 each being configured to expand the capture device 32 into a parachute-like structure 32, and to collapse the capture device 32 into a contracted condition (See FIG. 5). Configured between or across the struts may be mesh, knitted, or perforated material 66 to thereby define a parachute-like capture assembly. The mesh or knitted portion 66 is connected to the struts 38, 40 by conventional means, such as by sewing or gluing. The knitted or mesh portion 66 may form a cone-like configuration with its most distal end 68 defining the apex of the cone. It is to be recognized, however, that other basket configurations may also be employed. The parachute-like capture device 32 is characterized by providing structure which may be particularly useful in collecting matter in its hollow interior.

The mesh or knitted portion 66 can include micropores which permit blood flow or can be replaced with other materials such as impermeable or permeable elastomers. Additionally, the entire basket portion can be made of the same material which is laser cut to a desired configuration. The thinner walled material could be used to span the area between struts.

In a preferred embodiment of the present invention, the capture device 32 expands radially with respect to the elongate wire 24 into a generally parachute-like member having a proximal end and a distal end. As the elongate wire is distally advanced with respect to the catheter 50, the plurality of inner struts 38 and outer struts 40 expand to project the capture device 32 into a parachute-like frame.

As shown in FIGS. 4-7, in an expanded condition, the inner struts 38 and the outer struts 40 are configured in an alternative pattern where one inner strut 38 is interspersed between two outer struts 40. As the capture device 32 is collapsed by retracting the elongate wire 24 proximally within a catheter 50, the outer struts 40 having a slight helix configuration at a proximal region 70, rotate relative to the inner struts 38. The rotation of the outer struts 38 operates to fold the capture device 32, wherein the pleats 72 of the parachute are furled into a contracted condition. The relatively reduced cross-section of the folded capture device 32 allows the capture device to be more easily retracted into the delivery catheter 50 sheath without intrusion from the pleated folds 72.

It is to be recognized that all struts can include a slight helix configuration so that all struts shift radial position when the device is collapsed. In such a design, certain struts (e.g., outer struts) can be configured to shift a greater amount than other struts so that the desired furling of the pleats is accomplished.

The elongate wire 24 may include a conventional guidewire or other wire structure having similar properties. One material of choice may be Nitinol. The elongate wire outer diameter is such that it can easily slide within a lumen 78 of the catheter 50. Generally, the elongate wire 24 has a length greater than that of the catheter 50 so that its proximal end can be grasped by an operator and so that the elongate wire 24 can be advanced and withdrawn independently of the catheter 50.

The delivery catheter 50 can be any commercially available catheter that is made from any appropriate biologically compatible material. Typically, the catheter will have a single lumen 28 as constructed out of a flexible polymer material such as silicone, rubber, polyvinylchloride, polyeurothanes, polyesters, polytetrafluoro-ethylene and the like. The catheter has to be flexible enough and long enough to navigate through blood vessels to the occluded vessel where clots or other foreign bodies are located. Typically, the catheter will range in length from about 20 to about 175 centimeters. The outer diameter of the catheter can also vary. That is, the outer diameter will range from about 2 to about 10 F (1 F equals 0.013 inch). The inner diameter will range from about 1 to about 9 F.

The struts 38, 40 can also be made from any biologically compatible material, such as Nitinol. Although the device is intended to be self-expanding, structure can be provided to accomplish expansion in a device that is not self-expanding. In an embodiment where the elongate wire 24 defines a tubular structure, for example, an elongate member can be configured through the elongate wire (tube) 24 and placed into engagement with the distal end 68 of the capture device 32. Relative movement between the elongate member and elongate wire (tube) can accomplish the opening and closing of the capture device 50.

In use, the capture device 32 and catheter 50 are inserted into a patient's vasculature using conventional techniques, fluoroscopy or other conventional means. The elongate capture device 32 and catheter 50 are then advanced within a patient's vasculature to a location near the clot or foreign body to be extracted. Through relative movement between the catheter 50 and capture device 32, the capture device 32 is deployed beyond the catheter 50 and allowed to assume an expanded configuration. The capture device 32 is then placed or manipulated to gather the unwanted material and is retracted back within the catheter 50. Retraction of the device back within the catheter 50 is made easy due to the folding action accomplished by the interaction between the second set of struts 40 and the catheter 50. That is, when retracted, the second set of struts 40 engage a lumen defined by the catheter 40 to thereby compress the device into a small profile.

A method for refolding and atraumatically retracting an embolic capturing device after deployment into a vessel, includes providing a parachute-like capture device having a capturing structure operatively connected to an elongate wire. The capture device further includes a frame having a plurality of inner or first struts and a plurality of outer or second struts which expand radially, wherein the first and second struts having proximal and distal ends are configured in an alternative pattern where one first strut is dispersed between two second struts. In contracting the capture device by retracting the elongate wire proximally within a catheter, the second strut having a slight helix at the proximal end rotates relative to the first strut, thereby folding the parachute-like capture device into a reduced profile for retracting the device within the catheter.

It is also contemplated that the present invention can be used as a filter in a blood vessel. In such a situation, the above-described capture device is deployed within a blood vessel and held stationary for a period of time sufficient for the extractor to filter unwanted material from a patient's bloodstream.

Thus, a capture system is disclosed which allows for the removal of thromboembolic material and foreign bodies from a blood vessel. While several particular forms and applications of the invention have been illustrated and described, it will be apparent to those skilled in the art that many more modifications are possible without departing from the spirit and scope of the invention. The invention, therefore, is not to be restricted except in the spirit of claims appended hereto.

What is claimed is:

1. A medical device for capturing embolic or foreign material in a body vessel, comprising:
   an elongate wire having a proximal end and a distal end; and
   a filter device associated with the elongate wire, the filter device having an expanded position and a contracted position and including a support frame made from at least one structural member having a proximal end and a distal end, the structural member having a helical configuration when the filter device is placed in the contracted position, wherein the structural member defines a first portion and second portion of the filter device, at least one of the first portion or second portion having a substantially straight configuration when placed in the expanded position.

2. The medical device of claim 1, further including a capturing structure associated with one of the portions of the filter device.

3. The medical device of claim 2, wherein the capturing structure is a membrane having a proximal opening and a multiplicity of micropores which permit blood flow therethrough but prevent emboli from passing through.

4. The medical device of claim 2, further, the capturing structure comprising a mesh structure.

5. The medical device of claim 2, wherein the capturing structure expands radially with respect to the elongate wire into a generally parachute-like member having a proximal end and a distal end, wherein the proximal end is defined by an orifice through which blood can flow.

6. The medical device of claim 1, further including an elongate tubular member having a proximal end and a distal end, the filter device being positionable within the elongate tubular member to maintain the filter device in the contracted position.

7. The medical device of claim 6, wherein the support frame of the filter device is made from a self-expanding material.

8. The medical device of claim 7, wherein the support frame expands from the contracted position to the expanded position when the filter device is advanced from the lumen of the elongate tubular member.

9. The medical device of claim 1, wherein the at least one structural member is biased radially outward.

10. The medical device of claim 1, wherein the support frame is formed by a pair of structural members.

11. The medical device of claim 1, wherein the filter device can be moved along the length of the elongate wire.

12. A medical device for capturing embolic or foreign material in a vessel, comprising:

an elongate tubular member having a proximal end, a distal end and an internal lumen;

a filter device storable within the lumen of the elongate tubular member, the filter device including a plurality of structural members forming a support frame, the filter device having an expanded position and a contracted position when placed within the lumen of the elongate tubular member, the structural members forming the support frame assuming a helical configuration in the contracted position and being self-expandable into the expanded position when the filter device is advanced out of the lumen of the elongate tubular member, wherein the structural members define a first portion and second portion of the filter device, at least one of the first portion or second portion having a substantially straight configuration when placed in the expanded position.

13. The medical device of claim 12, further including a capturing structure associated with one of the portions of the filter device.

14. The medical device of claim 13, wherein the capturing structure is a membrane having a proximal opening and a multiplicity of micropores which permit blood flow therethrough but prevent emboli from passing through.

15. The medical device of claim 13, further, the capturing structure comprising a mesh structure.

16. The medical device of claim 13, wherein the capturing structure expands radially with respect to the elongate wire into a generally parachute-like member having a proximal end and a distal end, wherein the proximal end is defined by an orifice through which blood can flow.

17. The medical device of claim 12, further including an elongate member adapted to move the filter device out of the lumen of the elongate tubular member.

18. The medical device of claim 17, wherein the elongate tubular member is a microcatheter.

19. The medical device of claim 17, wherein the filter device is attached to the elongate member.

20. The medical device of claim 19, wherein the elongate member is a guide wire.

21. The medical device of claim 19, wherein the filter device is slidably movable along the length of the elongate member.

22. The medical device of claim 12, wherein each of the structural members have a first end and a second end, the first ends of the structural members being attached together and the second ends of the structural members being attached together.

23. The medical device of claim 22, wherein the structural members are configured in an alternating pattern when in the expanded position.

24. The medical device of claim 23, wherein the structural members are biased radially outward.

25. The medical device of claim 24, wherein the first ends and second ends of the structural members move away from each other during contraction.

26. A method for capturing emboli material or other particulates in a body vessel, comprising:

providing a medical device including (a) an elongate tubular member having a proximal end, a distal end and an internal lumen and (b) a filter device including a support frame having a plurality of structural members which expand radially from a contracted position, the filter device including a capturing structure attached to the support frame, the structural members forming the support frame assuming a helical configuration in the contracted position and being self-expandable into the expanded position when the filter device is advanced out of the lumen of the elongate tubular member, wherein the structural members define a first portion and second portion of the filter device, at least one of the first portion or second portion having a substantially straight configuration when placed in the expanded position;

placing the filter device into the lumen of the elongate member;

advancing the elongate tubular member into a body vessel;

moving the filter device out of the lumen of the tubular member; and capturing embolic material or other particulate in the body vessel in the capturing structure.

27. The method of claim 26, wherein each of the structural members have a proximal end and a distal end, the proximal ends being coupled together and the distal ends being coupled together.

28. The method of claim 26, wherein the filter device is moved out of the lumen of the elongate tubular member by an elongate member.

29. The method of claim 26, further including:

retrieving the embolic material or particulates from the body vessel.

\* \* \* \* \*